United States Patent [19]

Tahvonen et al.

[11] Patent Number: 5,968,504
[45] Date of Patent: Oct. 19, 1999

[54] **FUNGUS *GLIOCLADIUM CATENULATUM* FOR BIOLOGICAL CONTROL OF PLANT DISEASES**

[75] Inventors: Risto Tapio Tahvonen, Jokioinen; Milja Tuulikki Keskinen, Vantaa; Marja-Leena Lahdenperä, Helsinki; Pekka Tapani Seiskari, Kirkkonummi; Esa Petri Teperi, Hämeenlinna; Ulla Anita Tuominen, Espoo; Hanna Helena Avikainen, Jokioinen, all of Finland

[73] Assignee: Kemira Agro Oy, Helsinki, Finland

[21] Appl. No.: 08/809,666

[22] PCT Filed: Sep. 29, 1995

[86] PCT No.: PCT/FI95/00536

§ 371 Date: Jul. 14, 1997

§ 102(e) Date: Jul. 14, 1997

[87] PCT Pub. No.: WO96/10626

PCT Pub. Date: Apr. 11, 1996

[30] Foreign Application Priority Data

Sep. 30, 1994 [FI] Finland ..................... 944557

[51] Int. Cl.$^6$ .......................... A01N 25/00; A01N 63/00; C07C 1/02; C12N 1/00
[52] U.S. Cl. ..................... 424/93.5; 424/405; 435/254.1; 435/261; 435/262; 435/911
[58] Field of Search ................. 424/93.5, 405; 435/262, 254.1, 261, 911

[56] References Cited

U.S. PATENT DOCUMENTS

| | | | |
|---|---|---|---|
| 4,668,512 | 5/1987 | Lewis et al. | 424/93 |
| 4,724,147 | 2/1988 | Marios et al. | 424/93 |
| 4,818,530 | 4/1989 | Marios et al. | 424/93 |
| 4,996,157 | 2/1991 | Smith et al. | 435/254 |
| 5,068,105 | 11/1991 | Lewis et al. | 424/93 |
| 5,165,928 | 11/1992 | Smith et al. | 424/93 |
| 5,194,258 | 3/1993 | Paau et al. | 424/93 |
| 5,268,173 | 12/1993 | Howell et al. | 424/93 |
| 5,273,749 | 12/1993 | Bok et al. | 424/405 |
| 5,288,634 | 2/1994 | Harman et al. | 435/254.1 |
| 5,300,127 | 4/1994 | Williams | 47/57.6 |

FOREIGN PATENT DOCUMENTS

| | | |
|---|---|---|
| 387 640 | 9/1990 | European Pat. Off. . |
| 0 470 287 | 2/1992 | European Pat. Off. . |
| 79343 | 8/1989 | Finland . |
| WO 91/07869 | 6/1991 | WIPO . |
| WO 93/01923 | 2/1993 | WIPO . |

OTHER PUBLICATIONS

H.C. Huang, "*Gliocladium catenulatum:* hyperparasite of *Sclerotinia sclerotiorum* and Fusarium species," pp. 2243–2246, vol. 56, Canadian Journal of Botany (1978).

Gülay Turhan, "Mycoparasitism of *Alternaria alternata* by an Additional Eight Fungi Indicating the Existence of Further Unknown Candidates for Biological Control," pp. 283–292, vol. 138, Journal of J. Phytopathology (1993).

Andres A. Reyes, "Suppression of Fusarium and Pythium pea root rot by antagonistic microorganisms," pp. 23–29, vol. 66, Phytoprotection (1985).

Rodriguez–Kabana et al., "Effectiveness of Species of Gliocladium, Paecilomyces, and Verticillium for Control of *Meloidogyne arenaria* in field soil," one page abstract of journal article, Nematropica, vol 14(2) pp. 155–170 (1984).

B. Lacicowa et al., "Fungi of the genera Trichoderma and Gliocladium as mycoparasites of some bean pathogens ÄColletotrichum lindemuthianum Sacc. et. Magn., Rhizoctonia solani, Botrytis cinereaÄ," one page abstract of journal article, Ochrony Roslin, vol. 29(6) pp. 16–17 (1985).

B. Lacicowa et al., "Treatment of bean seeds in Trichoderma spp. and Gliocladium spp. against certain pathological fungi," one page abstract of journal article, Annual. Series E—Plant Protection, vol. 18(2) pp. 71–84 (1988).

Steinmetz et al., "Applicability of Different Formulations of Fungal Antagonists for the Control of Soil–Borne Diseases," New Approaches in Biological Control of Soil–Borne Diseases, Proceedings workshop, pp. 206–208, Copenhagen, Denmark Jun. 30–Jul. 4, 1991.

*Primary Examiner*—Leon B. Lankford, Jr.
*Assistant Examiner*—Deborah K. Ware
*Attorney, Agent, or Firm*—Marshall, O'Toole, Gerstein, Murray & Borun

[57] ABSTRACT

The present invention relates to biological control of plant diseases and concerns new *Gliocladium catenulatum* fungi and their use for controlling fungal infections in plants. The invention concerns also compositions comprising new strains of *Gliocladium catenulatum* and their use to said purpose.

15 Claims, No Drawings

FUNGUS *GLIOCLADIUM CATENULATUM* FOR BIOLOGICAL CONTROL OF PLANT DISEASES

FIELD OF THE INVENTION

The present invention relates to biological control of plant diseases and concerns specifically new microorganisms belonging to the genus Gliocladium as well as their use for controlling fungal infections in plants. The invention concerns also compositions comprising new Gliocladium strains and their use to said purpose.

BACKGROUND OF THE INVENTION

Cultivated crops are affected with various fungal, bacterial and viral diseases as well as a number of insect pests. Many cultivation technical, chemical and biological control methods have been developed in order to control these. The purpose of such methods is to prevent the qualitative and quantitative crop losses caused by plant diseases and other pests.

In general the term biological control of plant diseases means the control of plant pathogens by another organism, which is then called a biological control organism of plant diseases, and the preparation made thereof a biological control agent or a biopesticide. The mechanisms of the biological control of plant diseases do vary, and the effect is often based on the cooperative action of many different mechanisms. The control effect may be based on inhibitory chemical agents produced by the organism, sometimes the control organism parasitizes the pathogen or competes with it for growth space and/or the nutrients available.

The need of discovering new biological control agents has been increased by the fact that many of the traditional chemical pesticides have turned out to be deleterious to the environment and human beings. A disadvantage of the chemicals is also the fact that many pests have become resistant to one or even a number of pesticides. The development of resistance to biopesticides is instead improbable because the effect thereof is based on a number of mechanisms of different types. The chemicals usually affect faster and more effectively than biopesticides. Biopesticides for their part are often longer-acting than chemicals as their effect is based on a viable and reproducible microorganism.

The most important group of biopesticides are bacterial products targeted against insects. Bioinsecticides based on the bacterium *Bacillus thuringiensis* may be the most commonly used. A biofungicide based on the actinomycete Streptomyces being effective against a number of soil-borne and seed-borne fungal diseases of plants is produced in Finland. Fungi of the genus Trichoderma have also fungicidal activity.

Bacteria of the genus Pseudomonas, especially of the species *Pseudomonas fluorescens* have been studied a lot and nowadays a great amount of *P. fluorescens* strains are known which have fungicidal activity. See e.g. published patent applications WO 92/18613, FI 92 1722 and WO 90/01327, as well as EP-patent 228 457.

It is known that fungi of the genus Gliocladium have fungicidal activity. *Gliocladium virens* strains, especially the *G. virens* strain G1-3, have been described in patent literature. A problem in the use of this species has been, however, that nobody has been able to produce a formulation of this fungus, in which the viability of the fungus would keep on a satisfactory level during the storage of the formulation. In U.S. Pat. Nos. 4,668,512, 4,724,147 and 4,818,530 besides other fungal strains the use of *Gliocladium virens* strains is described in the preparation of biofungicidal formulations. Also in U.S. Pat. Nos. 5,165,928, 5,194,258 and 5,268,173 the use of *Gliocladium virens* strains as biofungicides has been described.

SUMMARY OF THE INVENTION

The present invention relates to *Gliocladium catenulatum* fungal strains which were found to be very active against a number of deleterious fungi.

The invention relates further to a biofungicidal composition prepared of a microbial strain comprising as an active ingredient the fungal strains belonging to the species *Gliocladium catenulatum* according to the invention and optionally additives or carriers conventional in the art as an appropriate formulation. Examples of such formulations are compositions suitable for seed dressing, powdered or granular compositions to be spread on growth substrates of the plants or liquid formulations to treat the soil.

DETAILED DESCRIPTION OF THE INVENTION

In the following the fungal strains of the invention as well as their isolation and characterization are described in detail. Further are described the formulation of the biofungicidal compositions formulated of these strains and characteristics thereof, and effectiveness tests with the isolated fungal strains and compositions prepared of them.

ISOLATION OF THE MICROORGANISMS

The soil samples, from where the fungal strains of the invention have been isolated, were collected in the years 1989 to 1991 from different parts of Finland, mainly from the research stations of MTT (Agricultural Research Center), from different soil types and different crop rotations using barley and wheat as bait plants. The samples were taken from the root layer (from the depth of 0 to 15 cm). Several subsamples were taken from each field, which were pooled to samples of 1 to 2 liters.

The isolations were made either by a dilution method (soil isolations) or a bait plant method (root isolations), the performance of which are described in detail hereinafter in the section Methods.

CHARACTERIZATION OF THE MICROORGANISMS

The fungal strains isolated from the soil samples were tested with the screening method described in the FI patent application 94 0463. Then five strains were found, which gave very good results. The strains, which were named *Gliocladium catenulatum* J1446, *Gliocladium catenulatum* M67-6, *Gliocladium catenulatum* J2734, *Gliocladium catenulatum* M2423 and *Gliocladium catenulatum* M3081, where characterized at DSM (Deutsche Sammlung von Mikroorganismen und Zellkulturen GmbH) in Germany. These strains have been deposited on May 19, 1994 according to the Budapest Treaty to the DSM depository by the accession numbers DSM 9212, DSM 9213, DSM 9214, DSM 9215 and DSM 9216 respectively The morphological characteristics of the microorganisms are the following:

Morphology: The primary conidiophores are Verticillium-like and the secondary ones Penicillium-like. Their length varies between 50 and 125 $\mu$M. They appear warted when observed directly, but smooth in liquid mounts. In the secondary conidiophores the conidia can keep bounded to each other to form long (even 150 μm) chains. The conidia are green and 4–7.5×3–4.5 μm in size. Hyaline chlamydospores can be present, terminal or intercalary, 7–10 μm in diameter.

Colony habit: On plates the colonies are spreading rather broadly. On malt extract agar they grow in ten days to the size of 2.5–3.5 cm in diameter at a temperature of 20° C. The colonies are otherwise like those of *G. roseum* but the conidial areas turn green (pale-olive) when they are 7 to 10 days old. In old cultivations the conidial areas are dark green. The reverse of the cultivations is colorless or yellowish.

From these strains formulations with reasonable shelf-life can be prepared, i.e. biofungicidal compositions of the invention, which are easy to spread onto plantations which require disease control. A formulation can be produced e.g. in the form of powder. Cultivation of a microbe can be started from an inoculum, which is a PDA pellet including spore suspension and having been kept at −80° C. The microbe can be cultivated either as a liquid culture or on a solid support. The nutrient medium comprises sugar, e.g. sucrose, and nitrogen as well as small amounts of other nutrients. A suitable nutrient medium for the cultivation is e.g. GYM (glucose 4 g/l, yeast extract 4 g/l, malt extract 10 g/l) or PDB (potato-dextrose-broth). The cultivation is performed from a little less than one week to well over a week. Then the fungus forms spores. The cell mass can be separated from the broth either by filtering through filter paper or by centrifuging. If liquid cultivation has been used a carrier, e.g. sucrose, milk powder, kaolin, starch, lignin and/or CMC (carboxymethylcellulose) is mixed to the cell mass. The mass is dried at room temperature and milled to powder.

METHODS

Isolations of the Microbes a) Dilution Method (Soil Isolations)

10 g of soil were mixed with 100 ml of 0.5% water agar (Bactoagar). $10^{-1}$ and $10^{-2}$ dilutions were made from the mixture into 0.5% water agar, as three replications. The dilutions were shaken (in water bath) in a shaker 20–30 min. 1 ml of the dilution was pipetted on an empty petri dish and 20 ml of Littman Oxgall Agar (LOA) was poured on. The dishes were incubated at room temperature for 3 to 7 days. The grown fungal colonies were isolated as pure onto PDA plates (Potato Dextrose Agar).

b) Bait Plant Method (Root Isolations)

Soil sample was placed in the wells of a serial pot plate (Vefi-VP 96 serial pot plate), 15 wells/soil sample (wells 40×40×60 mm). Wheat, barley and turnip rape were sown into the wells, 5 wells/species. Four seeds of wheat, four seeds of barley and 10–20 seeds of turnip rape per well were sown. The seeds were covered with sand. The seed and the surface of the soil were watered, alltogether under 10 ml/pot. Cultivation at the temperature of +15° C. After two weeks of cultivation the plants were picked up and washed in running water or cleaned up with a brush without water. From the roots small pieces were cut and they were put on plates. The media used: LOA (10 g peptone, 10 g dextrose, 15 g Bacto-Oxgall, 0.01 g B chrystal violet, 0.03 g streptomycin, 20 g agar, ad. 1000 ml water), PCNB (15 g peptone, 1 g $KH_2PO_4$, 0.5 g $MgSO_4.7H_2O$, 2 g Avicol, 3 ppm streptomycin, 20 g agar, ad. 1000 ml water) and PDA-Streptomycin (39 g PDA-preparation, 300 ppm streptomycin, ad. 1000 ml water). After a few days of incubation the fungi were transferred onto PDA plates.

The strains were stored by taking with a cork drill pellets from the PDA plates and freezing the pellets in ampoules (Nalgene 5000-0012, PP Sterile 1.2 ml) at −80° C.

The green house tests included in the screening method used in the selection of the strains were performed as described in FI patent application 94 0463 and these tests are briefly described hereafter.

Sand Test

Seeds of a cereal are sown on a sand layer. First mycelia and spores of the pathogen and then spores of the test fungus are pipetted in a water suspension on the seeds and to the growth substrate, whereafter the seeds are covered by sand. After two and a half weeks the intensity of the disease symptoms of the sprouts are examined (scale 0–5). From further experiments those fungi are rejected which do not affect the intensity of the disease or which prove to be pathogenic themselves.

Peat Test

A seed of a cereal is wetted in a spore suspension of a pathogen, and dried. After this the seed is wetted with the spore suspension of the test fungus, dried and sown. Steamed peat is used as growth substrate. After two and a half weeks of cultivation observations on the health of the sprouts are made. Fungal strains which clearly prevent the disease are taken to the field soil test.

Field Soil Tests

Grounded and wetted field soil is put in 1.5 l pots and 36 cereal seeds are sown into each pot. The seed treatments before sowing are made as in the peat test. E.g. three replicate pots are used in the test. The symptoms of the sprouts are examined after four weeks of cultivation.

Strains which are found good in these tests are taken to the field tests, which give the final certainty of the biopesticidal effect of the microbial isolates selected.

Pathogenicity of the Fungal Strains

Efficacy of the J1446 fungal strain in the control of plant diseases has been tested in a number of tests on eight plant species in total. None of the tests showed any detrimental effect of J1446 to the development of the plants although in some of the tests especially the seeds of the plants were treated, sometimes with quite high doses. On the basis of this it is evident that J1446 does not impede the development of the plants. To get additional verification a new series of tests was begun to show the efficacy of J1446 on 32 different plant species, bu no results of the same are not yet available. The other *Gliocladium catenulatum* strains of the invention have not been tested as broadly as J1446. In the efficacy tests in which said strains (J2734, M67-6, M2423 and M3081) have taken part these were not found to be pathogenic.

EXPERIMENTAL

The following experiments illustrate the utilization of the invention. In item (A) the preparation of the formulations made from the *Gliocladium catenulatum* strains of the invention, in item (B) the control efficacy results of the J1446 fungal strain against Rhizoctonia-, Pythium-, Alternaria- or Fusarium infection on cauliflower, cucumber, dill and wheat as a spore suspension and as different formulations, in item (C) the efficacy of the fungal strains against damping-off fungi (Rhizoctonia, Pythium, Fusarium, Phomopsis and Alternaria) on tomato, cauliflower, sugar beet, cucumber and lettuce, in item (D) the comparative tests by which the effect of the fungal strains of the invention, especially the strain J1446, and the effect of the commercial formulation, respectively, on the following pathogens: Fusarium and *Gaueumannomyces graminis* on barley and wheat, and in item (E) the mode of action by the strains are described.

(A) Preparation of the Formulations from the Fungal Strains

The powder formulations from the J1446 fungal strain were prepared as follows:

(a) Shake Cultivation

The cultivation was carried out in a 1 l erlenmeyer bottle having 0.5 l of nutrient medium, which included sucrose 4 g/l, yeast extract 4 g/l, malt extract 10 g/l and CMC 10 g/l. pH was not adjusted before sterilization in autoclave. As an inoculum an agar pellet (Potato dextrose agar medium) including spores was used which had been stored at −80° C. The speed of the shaker was 150 rpm, growth temperature was the room temperature (22–26° C.) and cultivation time 3 to 7 days. The cells were separated by centrifuging (9000 rpm, 20 min). To the cell mass one or more of the following materials were mixed: sucrose, milk powder, kaolin, starch, lignin and CMC.

| Formulation 1 | |
|---|---|
| cells | 40% (dry matter) |
| sucrose | 20%. |
| kaolin | 35%. |
| CMC (7% water soln.) | 5%. |

The mixture was dried at room temperature on open petri dishes in a fume chamber for 4 to 7 days. The thickness of the layer was 1 to 2 cm. The dried plates were milled to powder. The viability of the formulation was $10^7$ cfu/g powder. (cfu=colony forming units). cfu (colony forming units) is a unit which is used in the viability determination of microbes. The diluted microbe suspension is spread on agar plates and colonies are counted after a few days. When the dilution is known, the amount of colonies, i.e. the amount of the microbial cells in the original sample can be counted.

| Formulation 2 | |
|---|---|
| cells | 40% (dry matter) |
| milk powder | 40% |
| sucrose | 20% |

Drying and milling as above. The viability of the formulation was $10^7$ cfu/g powder.

| Formulation 3 | |
|---|---|
| cells | 40% (dry matter) |
| starch | 35% |
| sucrose | 20% |
| CMC (7% water soln.) | 5% |

Drying and milling as above. The viability of the formulation was $10^7$ cfu/g powder.

| Formulation 4 | |
|---|---|
| cells | 40% (dry matter) |
| lignin | 35% |
| sucrose | 20% |
| CMC (7% water soln.) | 5% |

Drying and milling as above. The viability of the formulation was $10^9$ cfu/g powder.

(b) Fermenter Cultivations

Formulation 5

The cultivations were carried out in Braun Biostat 10 and 30 l aerated fermenters, wherein the liquid volumes were 10 l and 25, l respectively. The nutrient media and conditions were similar to those of the shake flask cultivations. Cultivation time was 4 days and the separation and formulation as well as drying were made as above. The viability of the formulation after milling was $10^7$ to $10^8$ cfu/g powder.

(c) Cultivation on a Solid Medium

Formulation 6

J1446 strain was cultivated on a solid medium including silica carrier. The growth medium included 50 ml of Potato-Dextrose broth (Difco, 24 g PD-medium/l distilled water), 20 g of silica (Sipernat 22S, Degussa) and 0.2 g of $CaCO_3$ (p.a. Merck). The substrates were mixed in a beaker and autoclaved for 20 min at 120° C. The cooled medium was inoculated with 4 ml of of J1446 spore suspension which was obtained by scraping the spores from a PDA plate into sterile water.

The medium was transferred aseptically into petri dishes and incubated for 10 days at 16° C. until the fungus formed spores. After this the medium was dried in open petri dishes at room temperature for 2 days. The viability of the dried preparation was $7*10^7$ cfu/g.

From the other strains of the invention formulations can be prepared in a similar manner.

(B) Control Effect Results of the J1446 Fungal Strain, Use as Spore Suspensions and as Different Formulations In Tables 1 to 12 the results of the control effect experiments are given, which were made with the strain J1446 as follows.

Control of the fungus *Rhizoctonia solani* on cauliflower: In Table 1 the control effect of the fungal strain J1446 at two different temperatures is given, in Table 2 the difference in the effects of the J1446 preparations (several batches made by fermenters of different sizes) and plate cultivation can be seen, and in Table 3 the effect of the liquid fermented preparation with different amounts and modes of use is seen.

Control of the fungus Pythium: In Table 4 the effect of different preparations on cucumber using drench treatment is given, in Table 5 the control effect of the dry and liquid dressing on dill when using the liquid fermentation preparation is shown, and in Table 6 the effect of different concentrations on the control effect when using the drench treatment. Test plant is cucumber.

Control of the fungus *Alternaria brassicicola* on cauliflower: In Tables 7 and 8 the effect of the fungal strain J1446 as liquid dressing (2 different concentrations) at 4 different pH values are given, and in Table 9 the effect of different preparations when using liquid dressing is described. In Table 10 similarly the effects of the different preparations are shown when using liquid dressing, whereby the infection was stronger than in the test of Table 9.

Control of the fungus *Fusarium culmorum* on wheat on two different growth substrates: In Table 11 the control effect of the fungal strain cultivated on a plate and of a solid phase preparation when using liquid dressing. Temperature 15° C. Peat as growth substrate. The test described in Table 12 is similar exept that the growth substrate used was sand, whereby in addition to the artificial infection by F. culmorum there was also natural infection derived from the field soil.

TABLE 1

The control effect of J1446 fungal strain against the fungus *Rhizoctonia solani* on cauliflower at two different temperatures (20° C. and 25° C.).

| | Emergence % | | Disease index (0–3) | | Fresh weight g/replication | |
|---|---|---|---|---|---|---|
| | 20° C. | 25° C. | 20° C. | 25° C. | 20° C. | 25° C. |
| Healthy | 100 | 98 | 0.04 | 0.24 | 25.3 | 25.5 |
| Inoculated | 76 | 34 | 1.55 | 2.09 | 17.0 | 9.3 |
| J1446 liquid dressing $10^6$/ml | 98 | 82 | 0.52 | 1.08 | 23.2 | 21.7 |

Disease index
0 healthy
1 slightly diseased
2 strongly diseased
3 dead or unemerged

TABLE 2

Control effect of liquid fermented J1446 preparations against *Rhizoctonia solani* fungus on cauliflower

| Size of fermenter dm³ | Treatment | Emergence % | Disease index (0–3) | Fresh weight g/replication | Control effect % |
|---|---|---|---|---|---|
| | Healthy | 98 | 0.07 | 41.1 | |
| | Inoculated | 58 | 2.40 | 14.1 | |
| 10 | Liquid dressing $10^7$/ml [1] | 98 | 0.42 | 40.8 | 85 |
| 10 | Liquid dressing $10^6$/ml [2] | 94 | 0.51 | 40.7 | 81 |
| 30 | Liquid dressing $10^6$/ml [3] | 86 | 0.86 | 35.8 | 66 |
| — | Liquid dressing from a plate $10^6$/ml | 100 | 0.21 | 44.6 | 94 |

[1] mean of 3 batches
[2] mean of 5 batches
[3] mean of 2 batches

Disease index
0 healthy seedlings
1 slightly diseased seedlings
2 strongly diseased seedlings
3 dead seedlings and unemerged seeds

TABLE 3

The effect of liquid fermented J1446 preparation 2/94 ($7 \times 10^8$ cfu/g) against the fungus *Rhizoctonia solani* on cauliflower with different modes and amounts of use. Pot test, peat as growth substrate.

| Test member | Living seedlings (%) | Disease index (0–3) | Fresh weight g/replication | Control effect % |
|---|---|---|---|---|
| Healthy | 98 | 0.08 | 33.7 | |
| Inoculated | 52 | 2.48 | 14.3 | |
| J1446 liquid dressing $10^6$/ml | 96 | 0.18 | 36.7 | 96 |
| J1446 mixing treatment on the day of seeding 1 g/l peat | 87 | 0.76 | 30.1 | 72 |
| J1446 mixing treatment on the day of seeding 0.1 g/l peat | 90 | 1.33 | 28.4 | 48 |
| J1446 mixing treatment 1 week before seeding 1 g/l peat | 93 | 1.39 | 31.9 | 45 |
| J1446 mixing treatment 1 week before seeding 0.1 g/l peat | 93 | 0.53 | 34.3 | 81 |

Disease index
0 healthy seedlings
1 slightly diseased seedlings
2 strongly diseased seedlings
3 dead seedlings and unemerged seeds

TABLE 4

The effect of J1446 drench treatment ($10^6$/ml, 4 ml/plant) against the fungus Pythium on cucumber. Pot test, peat as growth substrate. R = shake cultivation in liquid, N = liquid fermented, KF = grown on solid phase and M = plain microbe grown on plate. The result of the shake cultivation as a mean of 2 batches and the result of liquid fermentation as a mean of 3 batches.

| Treatment | The amount of living seedlings (%) | Disease index (0–2) | Fresh weight g/replication |
|---|---|---|---|
| Healthy | 100 | 0.00 | 37.5 |
| Inoculated | 70 | 0.36 | 21.6 |
| J1446 R | 96 | 0.04 | 32.5 |
| J1446 N | 92 | 0.09 | 33.5 |
| J1446 KF | 90 | 0.10 | 31.7 |
| J1446 M | 98 | 0.02 | 35.4 |

Disease index
0 living seedlings
1 dead seedlings
2 unemerged

TABLE 5

The effect of J1446 dressing treatments against soil-borne fungus *Pythium sylvaticum* on dill. F = grown in 30 litre fermenter, sample 2/94 ($7 \times 10^8$ cfu/g).

| Test member | Emergence-% | Amount of all seedlings (%) | Size grading (0–4) |
|---|---|---|---|
| Healthy | 58.0 | 55.0 | 2.12 |
| Inoculated | 48.3 | 31.7 | 1.42 |
| J1446 F dry dressing 8 g/kg | 63.3 | 51.7 | 2.10 |
| J1446 F liquid dressing $10^6$/ml | 63.3 | 55.0 | 2.18 |

Size grading
4 the 4th foliage leaf of the seedling has begun to open or has been opened
3 the seedling has 3 proper foliage leaves
2 the seedling has 2 foliage leaves
1 the seedling has <2 foliage leaves
0 unemerged or dead

TABLE 6

The effect of J1446 drench treatment against soil-borne fungus Pythium in different concentrations. Cucumber as test plant. R = shake culture batch 57/93/1 7d ($1.7 \times 10^8$ cfu/g).

| Test member | The amount of healthy seedlings (%) | Disease index (0–2) | Fresh weight g/replication |
|---|---|---|---|
| Healthy | 98.0 | 0.04 | 17.4 |
| Inoculated | 66.0 | 0.36 | 9.8 |

TABLE 6-continued

The effect of J1446 drench treatment against soil-borne fungus Pythium in different concentrations. Cucumber as test plant. R = shake culture batch 57/93/1 7d (1.7 × .10⁸ cfu/g).

| Test member | The amount of healthy seedlings (%) | Disease index (0–2) | Fresh weight g/replication |
|---|---|---|---|
| J1446 R drench 10⁷/ml | 100.0 | 0.00 | 16.9 |
| J1446 R drench 10⁶/ml | 96.0 | 0.04 | 17.7 |
| J1446 R drench 10⁵/ml | 84.0 | 0.18 | 15.2 |

Disease index
0 healthy seedlings
1 dead seedlings
2 unemerged

TABLE 7

The control effect of J1446 fungal strain (liquid dressing 10⁵/ml) against *Alternaria brassicicola* damping-off on cauliflower. 4 pot tests in different pH values, peat as growth substrate.

| | Disease index (0–3) | | | Fresh weight g,replication | | |
|---|---|---|---|---|---|---|
| pH | Healthy | Inocul. | J1446 | Healthy | Inocul. | J1446 |
| 5.3 | 0.06 | 1.78 | 0.17 | 33.4 | 24.8 | 33.1 |
| 5.9 | 0.04 | 1.97 | 0.14 | 23.6 | 16.8 | 22.8 |
| 6.9 | 0.22 | 2.15 | 0.12 | 29.8 | 23.7 | 33.3 |
| 7.4 | 0.11 | 2.06 | 0.21 | 31.7 | 21.1 | 30.9 |

TABLE 8

The control effect of J1446 fungal strain (liquid dressing 10⁶/ml) against *Alternaria brassicicola* damping-off on cauliflower. 4 pot tests in different pH values, peat as growth substrate.

| | Disease index (0–3) | | | Fresh weight g/replication | | |
|---|---|---|---|---|---|---|
| pH | Healthy | Inocul. | J1446 | Healthy | Inocul. | J1446 |
| 5.6 | 0.10 | 2.25 | 0.13 | 33.8 | 19.8 | 33.7 |
| 6.0 | 0.08 | 1.96 | 0.15 | 35.7 | 26.7 | 35.7 |
| 6.2 | 0.06 | 2.31 | 0.07 | 32.1 | 22.8 | 33.5 |
| 6.4 | 0.03 | 2.40 | 0.05 | 32.9 | 21.5 | 32.8 |

Disease index
0 healthy
1 slightly diseased
2 strongly diseased
3 dead and unemerged

TABLE 9

The control effect of J1446 preparations against Alternaria fungus on cauliflower. R = shake cultivation in liquid, N = fermentation in liquid, KF = cultivated on solid phase, and M = plain microbe cultivated on a plate. The results of the shake cultivation as the mean of 2 batches and the results of liquid fermented as the mean of 4 batches. Pot test, peat as growth substrate.

| Treatment | Emergence-% | Disease index (0–3) | Fresh weight g/replication |
|---|---|---|---|
| Healthy | 96 | 0.15 | 34.2 |
| Inoculated | 55 | 1.91 | 26.8 |
| J1446 R liquid dressing 10⁶/ml | 97 | 0.14 | 34.4 |
| J1446 N liquid dressing 10⁶/ml | 97 | 0.23 | 33.9 |
| J1446 KF liquid dressing 10⁶/ml | 97 | 0.10 | 33.3 |
| J1446 M liquid dressing 10⁶/ml | 97 | 0.10 | 34.8 |

Disease index
0 healthy
1 slightly diseased
2 strongly diseased
3 dead or unemerged

TABLE 10

Control effect of J1446 preparations (liquid dressing 10⁶/ml) against *Alternaria brassicicola* fungus on cauliflower. R = shake cultivation in liquid, KF = cultivated on solid phase, M = plain microbe cultivated on a plate. The results of shake cultivation as a mean of 7 batches. Pot test, peat as growth substrate.

| | Emergence-% | Disease index (0–3) | Fresh weight g/replication |
|---|---|---|---|
| Healthy | 95 | 0.20 | 33.6 |
| Inoculated | 8 | 2.87 | 5.6 |
| J1446 R | 96 | 0.23 | 34.2 |
| J1446 KF | 95 | 0.19 | 33.2 |
| J1446 M | 96 | 0.19 | 33.2 |

Disease index
0 healthy
1 slightly diseased
2 strongly diseased
3 dead or unemerged

TABLE 11

The effect of J1446 (liquid dressing 10⁶/ml) against *Fusarium culmorum* fungus on Polkka wheat as the mean of three pot tests (pH 5.6, 6.3 and 7.0). Peat as growth substrate. Temperature 15° C. M = plain microbe cultivated on a plate, and KF = cultivated on solid phase (3.8 × 10⁸ cfu/g).

| Test member | Sprouting-% | Disease index (0–3) | Fresh weight g/replication |
|---|---|---|---|
| Healthy | 93.8 | 0.32 | 29.5 |
| Inoculated | 8.9 | 2.89 | 5.4 |
| J1446 M | 73.8 | 1.36 | 27.0 |
| J1446 KF 58/93 | 75.6 | 1.29 | 27.2 |

TABLE 12

Effect of J1446 (liquid dressing 10⁶/ml) against *Fusarium culmorum* fungus on Polkka wheat as the mean of five pot tests (pH 5.3, 6.5, 7.1, 7.4 and 8.0). Sand as growth substrate. Temperature 15° C. M = plain microbe cultivated on a plate, and KF = cultivated on solid phase.

| Test member | Sprouting-% | Disease index (0–3) | Fresh weight g/replication |
|---|---|---|---|
| Healthy | 82.9 | 1.25 | 45.5 |
| Inoculated | 48.5 | 2.09 | 34.2 |
| J1446 M | 59.5 | 1.54 | 41.7 |
| J1446 KF 58/93 | 61.9 | 1.70 | 43.0 |

Disease index
0 healthy
1 slightly diseased
2 strongly diseased
3 dead or unemerged (C) The Effect of the Fungal Strains of the Invention Against Damping-off Fungi
Diseases and test plants:
Alternaria: seed-borne; cauliflower
Rhizoctonia: soil-borne; cauliflower
Pythium: soil-borne; sugar beet, lettuce, cucumber
Fusarium: soil-borne; tomato Dilutions: 1 plate/liter peat, whereby the amount of spores is about $10^6$/ml peat.

Mixing and storage: The fungal mycelia and spores were scraped from a plate (age not less than 3 weeks) with a slide and mixed by Ultra Turrax with distilled water, 100 ml/liter of peat (1 plate/100 ml water/1 liter of peat), the suspension was mixed with peat and the peat was stored at room temperature for 1 day, 1 week, 2 weeks or 1 month depending on the test.

Peat: In all tests the peat was fertilized by using 800 g of dolomite lime and 150 g of peat Y-lannos/100 l of peat (Y-lannos=trade mark of a Finnish universal fertilizer), and steamed. The inoculation peat was prepared by mixing 1 PDA plate of pathogenic fungus with the agar with water using Ultra Turrax and by mixing the suspension with the steamed peat (1 PDA plate of fungus/100 ml of water/liter of peat). The peat was stored at room temperature. The contamination peat was mixed with the steamed peat for the tests in the proportion of 1:19 before the mixing of the antagonist suspension.

Performance

The cauliflower and sugar beet tests: (Rhizoctonia, Alternaria, Pythium) The seeds were sown into plastic pots of 0.5 liters, 25 seeds/pot. Five replications were used. The cultivation was taken place at the temperature of 18–20° C., in a continuous light of about 6000–8000 lux.

Analysis: Emerging of the seedlings was counted after 9 days from sowing. The dead ones were counted and discarded at two day's intervals until the end of the test. The test was stopped after about three weeks from sowing (18–22 days). Then the damages of the seedlings were analyzed in the scale of 0–3:
0=healthy
1=damping-off on cotyledon leaves
2=roots and the base of the seedling slightly diseased
3=the base of the seedling badly diseased, the seedling dead From the results the amount of healthy seedling was counted as percentage of sown seeds (the unemerged seeds were thus also taken into consideration). The dry weight of the seedling was also weighed (17 hours at 105° C.).

Dressing tests: The seeds of cauliflower were dressed with three antagonist concentrations: 1 plate of fungus/25 ml of water ($10^6$, where cfu $10^7$) and dilutions of this $10^{-1}$ (cfu $10^6$) and $10^{-2}$ (cfu $10^5$). For sugar beet dilutions of $10^0$ and $10^{-2}$ were used. 5 ml of suspension was pipetted on the seeds, which was let to affect for one minute. The seeds were dried on a filter paper until the next day, at which time they were sown. The performance and analysis of the test were carried out analogously with the other cabbage and sugar beet tests.

Tomato: In the tests 10 replications were used, each replication had one seedling. The seeds were sown into non-steamed peat.

Test 1: On the bottom of a 1 liter plastic pot a filter paper was placed, on which 10 g of contaminated peat was measured and the pot was filled with antagonist peat. When 12 days old the seedlings were planted in pots. The cultivation time was 2 months.

Analysis: A 10 cm piece was cut from the base of the stem and at the height of about one meter. The cutting surface was examined visually. If no browning of the vascular bundles was seen clearly, 0.5 cm thick pieces of the stem were placed on corn-streptomycin medium (4 pieces/plate). The media were examined after two weeks. The grading scale in the test was 0–5:
0=healthy base
1=visually no disease but in agar cultivations disease on base pieces
2=the base clearly brown (ocularly)
3=the base clearly diseased, on agar cultivations disease also at the height of 1 meter
4=disease visually also at the height of 1 meter
5=the plant w as dead.

Test 2: The initial cultivation as in test 1. The seedlings were planted when 15 days old into one liter pots in peat, wherein both contaminated peat (1:19) and antagonist suspension had been mixed. Cultivation for 47 days. Analysis: a piece of stem was cut from the base and at the height of 50 cm. Pieces of both of these were placed on corn-streptomycin media. The cultivations were examined after two weeks. In analysis the scale 0–4 was used:
0=healthy
1=on agar growth on base pieces
2=the disease detectable visually on the base
3=disease at 50 cm, growth decreased
4=the plant is dead Cucumber Pythium: 10 replications, 1 plant/replication. The seedlings were germinated in pure peat for 11 days, planted into contaminated and treated peat. The cultivation time after the treatment was 24 days, whereby the disease grade of the base and roots of the seedling were analyzed by the scale 0–5:
0=healthy
1=slightly diseased roots, the base healthy
2=roots and the base slightly damaged
3=roots and the base clearly diseased
4=roots almost dead, the base diseased
5=the plant is dead In addition, the length of the seedlings was measured and the dry weight was weighed.

Phomopsis: 3 replications, 3 plants in each. The pregerminated seeds were sown into 0.5 liter pots, on the bottom of which 10 g of contaminated peat was placed, and the pots were filled with antagonist peat. After 19 days the seedlings were transferred into 3 l pots into steamed peat. The seedlings were cultivated in artificial light at about 20° C. Additional fertilization was given 2 times a week. The test was stopped after three months from sowing.

Analysis: The disease grade of the cucumber shoots was examined in the scale 0–5:
0=healthy plant
1=in roots a few disease symptoms, the base healthy 2=roots slightly diseased, the base slightly damaged
3=roots and the base clearly damaged
4=the plant wilted, roots sparse, the base brown
5=the plant is dead Lettuce: The seeds (35) were sown onto a serial pot plate (Vefi-VP 96) into peat contaminated with Pythium and treated with an antagonist. The seedlings were cultivated for 6 weeks, at which time the health and the thickness of the seedling roots were analyzed in scale 0–3:
0=roots healthy
1=slightly thinned
2=clearly thinned and browned roots
3=the seedling almost dead.

The fresh weight of the seedlings was weighed.

J1446 Powder Tests

Amount of application tests:

Test plants: cauliflower and sugar beet.

Amounts of application:

1 g J1446 powder/liter of peat
0.5 g/liter of peat
0.1 g/liter of peat
0.05 g/liter of peat
0.01 g/liter of peat
0.001 g/liter of peat.

The powder was mixed with water (100 ml/liter of peat) using Ultra Turrax, it was let to stand for one hour and mixed with peat. Sowing, the management and analysis of the test were carried out similarly with the other cauliflower and sugar beet tests.

Results

TABLE 13

The effect of the antagonists mixed with peat against Pythium damping-off of sugar beet. Concentration 1 plate/litre of peat (cfu ca $10^5$–$10^6$/ml of peat). The tests were sown one day and one week or one month after the antagonist treatment.

| | Test 3/93 | | Test 6/93 | | Test 7/93 | | |
|---|---|---|---|---|---|---|---|
| Test member | 1 day | 1 week | 1 day | 1 month | 1 day | 1 week | Mean |
| | Healthy seedlings of sown, % | | | | | | |
| Healthy control | 93.6 | 95.2 | 94.4 | 88.8 | 80.0 | — | 90.4 |
| Diseased control | 11.2 | 16.0 | 27.2 | 21.6 | 16.8 | 52.0 | 24.1 |
| J1446 | 96.8 | 92.0 | 74.4 | 63.2 | 66.4 | 67.2 | 76.7 |

TABLE 14

The effect of the antagonists mixed with peat against Pythium damping-off of sugar beet. Concentration 1 plate/litre of peat (cfu ca $10^5$–$10^6$/ml of peat). The tests were sown one day and one month after the antagonist treatment.

| | Test 14/93 | | Test 18/93 | | |
|---|---|---|---|---|---|
| Test member | 1 day | 1 day | 1 day | 1 month | Mean |
| | Healthy seedlings of sown, % | | | | |
| Healthy control | 72.8 | 81.6 | 84.8 | 75.2 | 78.6 |
| Diseased control | 56.8 | 32.8 | 41.6 | 20.0 | 37.8 |
| J1446 | 78.4 | 62.4 | 62.4 | 84.0 | 71.8 |
| M67-6 | 72.0 | 52.8 | 65.6 | 66.4 | 64.2 |
| M3081 | 76.0 | 56.8 | 72.0 | 60.0 | 66.2 |
| M2423 | 76.8 | 55.2 | 67.2 | 72.8 | 68.0 |
| J2734 | — | — | 68.8 | 68.8 | 68.8 |

TABLE 15

The effect of antagonists mixed with peat against Pythium damping-off of sugar beet. Concentration 1 plate/litre of peat (cfu ca $10^5$–$10^6$/ml of peat). The tests were sown one day and one month after the antagonist treatment.

| | Test 2/94 | | Test 10/94 | | |
|---|---|---|---|---|---|
| Test member | 1 day | 1 month | 1 day | 1 month | Mean |
| | Healthy seedlings of sown, % | | | | |
| Healthy control | 82.4 | 88.0 | 96.0 | 84.8 | 87.8 |
| Diseased control | 33.6 | 44.0 | 38.4 | 36.8 | 38.2 |
| J1446 | 55.2 | 71.2 | 80.0 | 70.4 | 69.2 |
| M67-6 | 64.8 | 83.2 | 72.0 | 63.2 | 70.8 |
| J2734 | 73.6 | 79.2 | 66.4 | 63.2 | 70.6 |
| M3081 | 73.6 | 75.2 | 69.6 | 64.8 | 70.8 |
| M2423 | 72.0 | 76.0 | 55.2 | 46.4 | 62.4 |

TABLE 16

The effect of antagonists mixed with peat against Pythium damping-off of sugar beet. Concentration 1 plate/litre of peat (cfu ca $10^5$–$10^6$/ml of peat). The tests were sown one day and one month after the antagonist treatment.

| | Test 2/94 | | Test 10/94 | | |
|---|---|---|---|---|---|
| Test member | 1 day | 1 month | 1 day | 1 month | Mean |
| | Dry weight of seedlings in all, g | | | | |
| Healthy control | 0.86 | 0.94 | 1.59 | 1.07 | 1.11 |
| Diseased control | 0.86 | 1.32 | 1.39 | 0.70 | 1.07 |
| J1446 | 1.03 | 1.54 | 1.66 | 1.22 | 1.36 |
| M67-6 | 0.98 | 1.52 | 1.68 | 1.11 | 1.33 |
| J2734 | 1.07 | 1.58 | 1.52 | 1.11 | 1.32 |
| M3081 | 1.14 | 1.55 | 1.70 | 1.14 | 1.38 |
| M2423 | 1.01 | 1.59 | 1.42 | 1.03 | 1.26 |

TABLE 17

The effect of antagonists mixed with peat against soil-borne Rhizoctonia damping-off of cauliflower. Concentration 1 plate/liter of peat (cfu ca $10^5$–$10^6$/ml of peat). The tests were sown one day and one week or two weeks after the antagonist treatment.

| | Healthy seedlings of sown, % | | | | | | |
|---|---|---|---|---|---|---|---|
| | Test 2/93 | | Test 5/93 | | Test 8/93 | | |
| Test member | 1 day | 1 week | 1 day | 2 weeks | 1 day | 1 week | Mean |
| Healthy contr. | 76.8 | 74.4 | 90.4 | 87.2 | 87.2 | 57.6 | 78.9 |
| Diseas. contr. | 15.2 | 46.4 | 17.6 | 41.6 | 12.0 | 15.2 | 24.7 |
| J1446 | 61.6 | 66.4 | 40.0 | 65.6 | 60.0 | 43.2 | 56.1 |

TABLE 18

The effect of antagonists mixed with peat against soil-borne Rhizoctonia damping-off of cauliflower. Concentration 1 plate/liter of peat (cfu ca $10^5$–$10^6$/ml of peat). The tests were sown one day and one month after the antagonist treatment.

| | Healthy seedlings of sown, % | | | | |
|---|---|---|---|---|---|
| | Test 3/94 | | Test 11/94 | | |
| Test member | 1 day | 1 month | 1 day | 1 month | Mean |
| Healthy control | 88.8 | 89.6 | 92.4 | 81.6 | 88.1 |
| Diseased control | 32.0 | 47.2 | 41.6 | 20.8 | 35.4 |

TABLE 18-continued

The effect of antagonists mixed with peat
against soil-borne Rhizoctonia damping-off of cauliflower.
Concentration 1 plate/liter of peat (cfu ca $10^5$–$10^6$/ml
of peat). The tests were sown one day and one month after
the antagonist treatment.

| | Healthy seedlings of sown, % | | | | |
|---|---|---|---|---|---|
| | Test 3/94 | | Test 11/94 | | |
| Test member | 1 day | 1 month | 1 day | 1 month | Mean |
| J1446 | 68.0 | 70.4 | 75.2 | 80.8 | 73.6 |
| M67-6 | 73.6 | 75.2 | 66.4 | 64.0 | 69.8 |
| J2734 | 30.4 | 83.2 | 68.8 | 68.0 | 62.6 |
| M3081 | 35.2 | 66.4 | 64.0 | 72.0 | 59.4 |
| M2423 | 67.2 | 73.6 | 63.2 | 68.0 | 68.0 |

TABLE 19

The effect of antagonists mixed with peat against Rhizoctonia
damping-off of cauliflower. Concentration 1 plate/liter of
peat (cfu ca $10^5$–$10^6$/ml of peat). The tests
were sown one day and one month after the antagonist treatment.

| | Dry weight of the seedlings in all, g | | | | |
|---|---|---|---|---|---|
| | Test 3/94 | | Test 11/94 | | |
| Test member | 1 day | 1 month | 1 day | 1 month | Mean |
| Healthy control | 1.17 | 0.87 | 1.59 | 0.70 | 1.08 |
| Diseased control | 0.87 | 0.75 | 1.39 | 0.47 | 0.87 |
| J1446 | 1.18 | 0.88 | 1.59 | 0.73 | 1.10 |
| M67-6 | 1.33 | 0.92 | 1.50 | 0.68 | 1.11 |
| J2734 | 0.61 | 0.98 | 1.47 | 0.69 | 0.94 |
| M3081 | 0.58 | 0.80 | 1.48 | 0.74 | 0.90 |
| M2423 | 1.06 | 0.96 | 1.49 | 0.62 | 1.03 |

TABLE 20

The effect of antagonists mixed with peat against seed-borne
Alternaria damping-off on cauliflower. Concentration 1 plate/liter
of peat (cfu ca $10^6$/ml of peat).

| Test member | Healthy, % | Disease index, 0–3 |
|---|---|---|
| Healthy control | 95.3 | 0.19 |
| Diseased control | 3.8 | 2.81 |
| J1446 | 89.8 | 0.67 |

TABLE 21

The effect of antagonist dressing against
soil-borne Rhizoctonia and Pythium diseases.

| | Healthy seedlings of sown, % | | | |
|---|---|---|---|---|
| | Concentration (cfu/ml of solution) | | | |
| Test member | $10^7$ | $10^6$ | $10^5$ | Mean |
| Rhizoctonia, cauliflower | | | | |
| Healthy contr. | 79.2 | | | |
| Diseased contr. | 34.4 | | | |
| J1446 | 72.8 | 63.2 | 64.8 | 66.9 |
| J2734 | 57.6 | 53.6 | 64.0 | 58.4 |
| Pythium, sugar beet | | | | |
| Healthy contr. | 88.8 | | | |
| Diseased contr. | 57.6 | | | |
| J1446 | 74.4 | — | 72.8 | 73.6 |

TABLE 21-continued

The effect of antagonist dressing against
soil-borne Rhizoctonia and Pythium diseases.

| | Healthy seedlings of sown, % | | | |
|---|---|---|---|---|
| | Concentration (cfu/ml of solution) | | | |
| Test member | $10^7$ | $10^6$ | $10^5$ | Mean |
| J2734 | 67.2 | — | 74.4 | 70.8 |
| Mycostop, (5 g/kg) | 53.6 | | | |

TABLE 22

The effect of antagonists mixed with peat against
the fungus Fusarium on tomato. Concentration 1 plate/liter
of peat (cfu ca $10^6$/ml of peat).

| | Disease index 0–4 | |
|---|---|---|
| Test member | Test 1 | Test 2 |
| Healthy control | 0.1 | 0.1 |
| Diseased control | 3.1 | 1.5 |
| J1446 | 1.9 | 0.6 |
| Other antagonists | 1.0–3.0 | 0.6–1.0 |

TABLE 23

The effect of antagonists mixed with peat against
Pythium disease of lettuce. Concentration 1 plate/liter
of peat (cfu ca $10^5$–$10^6$/ml of peat).

| Test member | Healthy, % | Fresh weight, g |
|---|---|---|
| Healthy control | 86.1 | 5.5 |
| Diseased control | 83.4 | 5.0 |
| Chemical dressing | 82.0 | 4.5 |
| J1446 | 83.3 | 5.5 |
| Other antagonists | 80.2–89.0 | 4.5–5.9 |

TABLE 24

The antagonists mixed with peat against Phomopsis
disease of cucumber. Concentration 1 plate/liter of peat
(cfu ca $10^6$/ml of peat).

| Test member | Disease index, 0–5 |
|---|---|
| Healthy control | 0.07 |
| Diseased control | 1.67 |
| J1446 | 1.07 |
| Other antagonists | 1.0–1.56 |

TABLE 25

The effect of J1446 powder against Rhizoctonia
damping-off of cauliflower. The powder was mixed
with peat as a water suspension.

| Test member powder g/liter of peat | Emerged % | Dry weight of seedlings in all g | Healthy seedlings of sown % | Dead % |
|---|---|---|---|---|
| Healthy control | 94.4 | 0.79 | 92.0 | 1.6 |
| Diseased control | 79.2 | 0.49 | 36.0 | 40.8 |
| J1446, fungal susp. | 91.2 | 0.74 | 71.2 | 15.2 |
| 1 g/l | 92.0 | 0.80 | 80.0 | 8.0 |
| 0.5 g/l | 92.8 | 0.78 | 75.2 | 7.2 |

TABLE 25-continued

The effect of J1446 powder against Rhizoctonia damping-off of cauliflower. The powder was mixed with peat as a water suspension.

| Test member powder g/liter of peat | Emerged % | Dry weight of seedlings in all g | Healthy seedlings of sown % | Dead % |
|---|---|---|---|---|
| 0.1 g/l | 88.0 | 0.68 | 57.6 | 20.8 |
| 0.05 g/l | 89.6 | 0.69 | 56.0 | 23.2 |
| 0.01 g/l | 84.8 | 0.48 | 36.8 | 39.2 |
| 0.001 g/l | 82.4 | 0.47 | 28.0 | 46.4 |

TABLE 26

The effect of J1446 powder against Pythium damping-off of sugar beet. The powder was mixed with peat as a water suspension.

| Test member powder g/liter of peat | Emerged % | Dry weight of seedlings in all g | Healthy seedlings of sown % | Dead % |
|---|---|---|---|---|
| Healthy control | 91.2 | 0.74 | 89.6 | 0.0 |
| Diseased control | 63.2 | 0.52 | 59.2 | 1.6 |
| J1446, fungal susp. | 86.4 | 0.71 | 81.6 | 0.0 |
| 1 g/l | 80.0 | 0.70 | 73.6 | 0.8 |
| 0.5 g/l | 73.6 | 0.61 | 70.4 | 1.6 |
| 0.1 g/l | 72.8 | 0.59 | 64.8 | 0.8 |
| 0.05 g/l | 79.2 | 0.62 | 76.0 | 0.0 |
| 0.01 g/l | 66.4 | 0.52 | 60.0 | 3.2 |
| 0.001 g/l | 72.8 | 0.63 | 68.8 | 0.0 |

(D) Comparison of the J1446 Isolate and Commercial Preparations in Greenhouse and Field Trials (a) Selection Tests With J1446 Against The Fungus *Fusarium Culmorum*

Sand test: J1446 obtained the grades 0, 0, 0, 0, 0 and 1 and was taken to the next test steps.

Peat Test

| | |
|---|---|
| Healthy control | 2 diseased |
| Fusarium-control | 42 diseased |
| F. c. and basic suspension (F0) | 0 diseased |
| F. c. and $10^{-2}$ dilution (F2) | 2 diseased |

| | Percentage of diseased sprouts |
|---|---|
| healthy control | 49 |
| Fusarium-control | 94 |
| Baytan I dressing | 37 |
| Tayssato S dressing | 60 |
| J1446 | 57 |

(b) Greenhouse and Field Soil Tests with J1446

TABLE 27

Greenhouse test with naturally contaminated (*Fusarium nivale*) barley

| | Percentage of diseased sprouts |
|---|---|
| Untreated | 74 |
| Baytan I dressing | 14 |
| J1446 | 16 |

TABLE 28

Field trial with artificially infected (*Fusarium culmorum*) wheat in the summer 1992

| | sprouts (no./row meter) | percentage of badly diseased sprouts | yield (kg/ha) |
|---|---|---|---|
| healthy seed | 44 | 15 | 2660 |
| untreated | 11 | 59 | 1000 |
| Baytan I dressing | 37 | 11 | 2630 |
| J1446 | 37 | 29 | 2430 |

TABLE 29

Field trial with naturally contaminated (*Fusarium nivale*) barley in the summer 1992

| | sprouts (no./row meter) | percentage of badly diseased sprouts | yield (kg/ha) |
|---|---|---|---|
| untreated | 36 | 26 | 4740 |
| Baytan I dressing | 35 | 11 | 5370 |
| J1446 | 39 | 12 | 5240 |

TABLE 30

Field trial with artificially infected (*F. culmorum*) wheat in the summer 1993. Square size was one row of 1.4 m

| | number of healthy sprouts/row |
|---|---|
| untreated | 6 |
| Baytan I dressing | 59 |
| J1446 | 56 |
| other strains tested | 30–68 |

TABLE 31

Field trial with 'naturally contaminated' (*F. culmorum*) wheat in the summer 1993. The seed were produced in the previous summer and infected during blooming with Fusarium conidial suspension. Differences between yield results are not statistically significant.

| | sprouts (no./row meter) | percentage of badly diseased sprouts | yield (kg/ha) |
|---|---|---|---|
| untreated | 34 | 28 | 5080 |
| Baytan I dressing | 44 | 2 | 5140 |
| J1446 | 44 | 7 | 4800 |
| other strains tested | 33–48 | 5–18 | 4860–5360 |

TABLE 32

Field trial against soil-borne foot rot causes (Fusarium spp./ *Gaueumannomyces graminis*) on wheat in the summer 1993

| | sprouts (no./ $m^2$ | percentage of damaged foots in sprouts | percentage of damaged roots in sprouts | yield (kg/ha) |
|---|---|---|---|---|
| untreated | 310 | 11 | 72 | 3830 |

TABLE 32-continued

Field trial against soil-borne foot rot causes (Fusarium spp./ Gaueumannomyces graminis) on wheat in the summer 1993

|  | sprouts (no./ m$^2$ | percentage of damaged foots in sprouts | percentage of damaged roots in sprouts | yield (kg/ha) |
|---|---|---|---|---|
| Baytan I dressing | 305 | 3 | 44 | 3910 |
| J1446 | 415 | 4 | 54 | 4080 |

(E) The Mechanism of Action of the Strains

The detection of the ways the by which the *Gliocladium catenulatum* fungal strains of the invention act on other fungi, have only begun. For the present we have nothing but microscope observations of the interaction of the mycelia in double cultivations, in which one isolate of the following fungi was cultivated with the fungal strain J1446: *Rhizoctonia solani*, *Fusarium culmorum* and *Pythium sp*. Mycelia of all of these plant pathogenic fungi begin to degrade when the mycelia of J1446 fungal strain grow near them. First large vacuoles are formed in the cells, then the cells empty and finally the cell walls degrade. This kind of reactions are evidently due to antibiotic or enzyme like substances which J1446 secrete to its environment. Obviously *R solani* is most sensitive of said fungi to the substances J1446 produce. On thin nutrient media the growth of the colonies of this fungus stops totally near the colonies of J1446, and as a consequence of this a narrow inhibition zone can be observed with naked eye. A part of the mycelia of all of the three fungi studied remain undegraded before the contact of the mycelia. Also these seem to degrade later on, when the mycelia of the fungal strain J1446 fold around them. The strength of the folding seems to depend on the growth medium used. The mycelia of the fungal strain J1446 have not been noticed to penetrate into the mycelia of other fungi.

The Interpretation of the Results

The *Gliocladium catenulatum* fungal strains which are the object of the invention have proven to be promising to be used in the biological control of plant diseases. The possible use of the strain J1446 has been detected most of all. It effects well against three very common soil-borne causes of damping-off: *Rhizoctonia solani*, *Pythium* and *Fusarium* fungi. Additionally, good results have been obtained with the same in the control of seed-borne diseases cause by the fungi Alternaria and Fusarium. With the fungal strains and formulations of the invention good results have been obtained by amounts of use which evidently are realistic in the cultivations in practice. It is also very promising that when mixed with the growth medium they have in tests kept their ability to control soil-borne diseases for long times.

According to the observations so far it seems that the fungal strains of the invention would even promote the emergence and growth of the plants and improve their quality. The treatment of the growth medium with these strains has also been noticed to decrease the growth of mold which are as such harmless, which promotes the emergence of plants with small seed and which sprout slowly.

Deposited Microorganisms

The following fungal strains were deposited in the DSM depository (Deutsche Sammlung von Mikroorganismen und Zellkulturen GmbH), Mascheroder Weg 1b, Braunschweig, D-38124 Germany.

| Microorganism | Accession number | Deposit date |
|---|---|---|
| *Gliocladium catenulatum* J1446 | DSM 9212 | 19 May 1994 |
| *Gliocladium catenulatum* M67-6 | DSM 9213 | 19 May 1994 |
| *Gliocladium catenulatum* J2734 | DSM 9214 | 19 May 1994 |
| *Gliocladium catenulatum* M2423 | DSM 9215 | 19 May 1994 |
| *Gliocladium catenulatum* M3081 | DSM 9216 | 19 May 1994 |

We claim:

1. A biologically pure culture of *Gliocladium catenulatum* J1446 (DSM 9212).

2. A biologically pure culture of *Gliocladium catenulatum* M67-6 (DSM 9213).

3. A biologically pure culture of *Gliocladium catenulatum* J2734 (DSM 9214).

4. A biologically pure culture of *Gliocladium catenulatum* M2423 (DSM 9215).

5. A biologically pure culture of *Gliocladium catenulatum* M3081 (DSM 9216).

6. A biofungicidal substance comprising a *Gliocladium catenulatum* fungal strain selected from the group consisting of DSM 9212, DSM 9213, DSM 9214, DSM 9215 and DSM 9216.

7. A method for inhibiting a fungal infection in a plant, which comprises applying to the plant or seeds thereof a substance according to claim 5 or adding the same into the growth substrate before or after sowing the seeds.

8. A stable biofungicidal composition with a wide spectrum, being effective both in greenhouse and field cultivations against both seed-borne and soil-borne diseases, the composition comprising a *Gliocladium catenulatum* fungal strain and carriers, and optionally at least one additive, wherein the *Gliocladium catenulatum* fungal strain is selected from the group consisting of *Gliocladium catenulatum* J1446, *Gliocladium catenulatum* M67-6, *Gliocladium catenulatum* J2734, *Gliocladium catenulatum* M2423, and *Gliocladium catenulatum* M3081.

9. The composition according to claim 8 wherein as carriers and additives one or more of the following are used: silica, kaolin, milk powder, carboxymethyl cellulose, sucrose, lignin and starch.

10. The composition according to any one of the claim 8 which is prepared by (a) cultivating a *Gliocladium catenulatum* fungal strain in a suitable growth medium, separating the cell mass and adding thereto carriers and/or additives, drying the mass obtained and milling it to powder, or (b) cultivating a *Gliocladium catenulatum* fungal strain in a suitable growth medium with silica and optionally adding thereto carriers and/or additives, drying the mass obtained and milling it into powder.

11. A method for inhibiting a fungal infection in a plant, which comprises applying to the plant or seeds thereof a composition according to claim 8, or adding the same into the growth substrate before or after sowing the seeds.

12. A method of controlling disease in a plant comprising the step of administering to the plant or seed(s) thereof a *Gliocladium catenulatum* strain selection from the group consisting of *Gliocladium catenulatum* J1446 (DSM 9212), *Gliocladium catenulatum* M67-6 (DSM 9213), *Gliocladium catenulatum* J2734 (DSM 9214), *Gliocladium catenulatum* M2423 (DSM 9215), and *Gliocladium catenulatum* M3081 (DSM 9216).

13. The method of claim 12 wherein the plant disease is a disease caused by a pathogen selected from the group consisting of Rhizoctonia, Pythium, Alternaria, Fusarium, Phomopsis, and Gaeumannomyces.

14. A method of controlling disease in a plant comprising the step of introducing into the growth medium containing said plant a *Gliocladium catenulatum* strain selected from the group consisting of *Gliocladium catenulatum* J 1446 (DSM 9212), *Gliocladium catenulatum* M67-6 (DSM 9213), *Gliocladium catenulatum* J2734 (DSM 9214), *Gliocladium catenulatum* M2423 (DSM 9215), and *Gliocladium catenulatum* M3081 (DSM 9216).

15. The method of claim 14 wherein the plant disease is a disease caused by a pathogen selected from the group consisting of Rhizoctonia, Pythium, Alternaria, Fusarium, Phomopsis, and Gaeumannomyces.

* * * * *